United States Patent [19]

Poncept

[11] Patent Number: 4,545,237
[45] Date of Patent: Oct. 8, 1985

[54] APPARATUS FOR BLOOD ANALYSIS

[76] Inventor: Gérard Poncept, 10, Chemin de Dalibray, Gaillonnet par Seraincourt, 95450-Vigny, France

[21] Appl. No.: 575,927

[22] Filed: Feb. 1, 1984

[30] Foreign Application Priority Data

Feb. 2, 1983 [FR] France ............................. 83 01644

[51] Int. Cl.⁴ ..................... G01N 15/04; G01N 33/48
[52] U.S. Cl. .................................... 73/61.4; 141/113; 422/73; 436/70
[58] Field of Search ........................... 73/61.4; 436/70; 422/68, 73, 103, 102, 99; 53/264, 268, 319, 489; 141/1, 59, 113, 275, 284, 237

[56] References Cited

U.S. PATENT DOCUMENTS

| | | | |
|---|---|---|---|
| 2,729,971 | 1/1956 | Stein | 73/61.4 |
| 3,329,179 | 7/1967 | Abel | 141/284 |
| 3,373,601 | 3/1968 | Monn | 73/61.4 |
| 3,827,286 | 8/1974 | Bond et al. | 73/61.4 |
| 4,197,735 | 4/1980 | Munzer et al. | 73/61.4 |

Primary Examiner—Barry S. Richman
Assistant Examiner—Robert J. Hill, Jr.
Attorney, Agent, or Firm—Brisebois & Kruger

[57] ABSTRACT

An apparatus for blood analysis to determine the rate of corpuscle sedimentation. The apparatus has a first support (1) with several graduated tubes (4) open at both ends and held vertically in spaced relation on the first support. The tubes (4) have enlarged lower ends (4b) which can diverge. A second support (2) has blood sample containers (13) of larger diameter than the vertical tubes on the first support. The containers (13) are spaced apart on the said second support, the same distance as the tubes on the first support so the containers are respectively, vertically below the tubes. Sealing and flow inducing members engage in the diverging lower ends (4b) of the respective tubes. The support means (1, 2) are movable with respect to each other between a first position in which the tubes are vertically above the containers, and a second position in which the lower ends of the tubes are immersed in the containers. The sealing and flow inducing members are mounted on the first support for simultaneous movement between a lower position away from the tubes and an upper position engaging within the enlarged ends of the tubes. The movement of the sealing members into engagement with the interior of the tubes causes a predetermined quantity of blood to be forced upwardly into the smaller diameter graduated portions of each tube to permit determining the sedimentation rates of the different samples.

10 Claims, 6 Drawing Figures

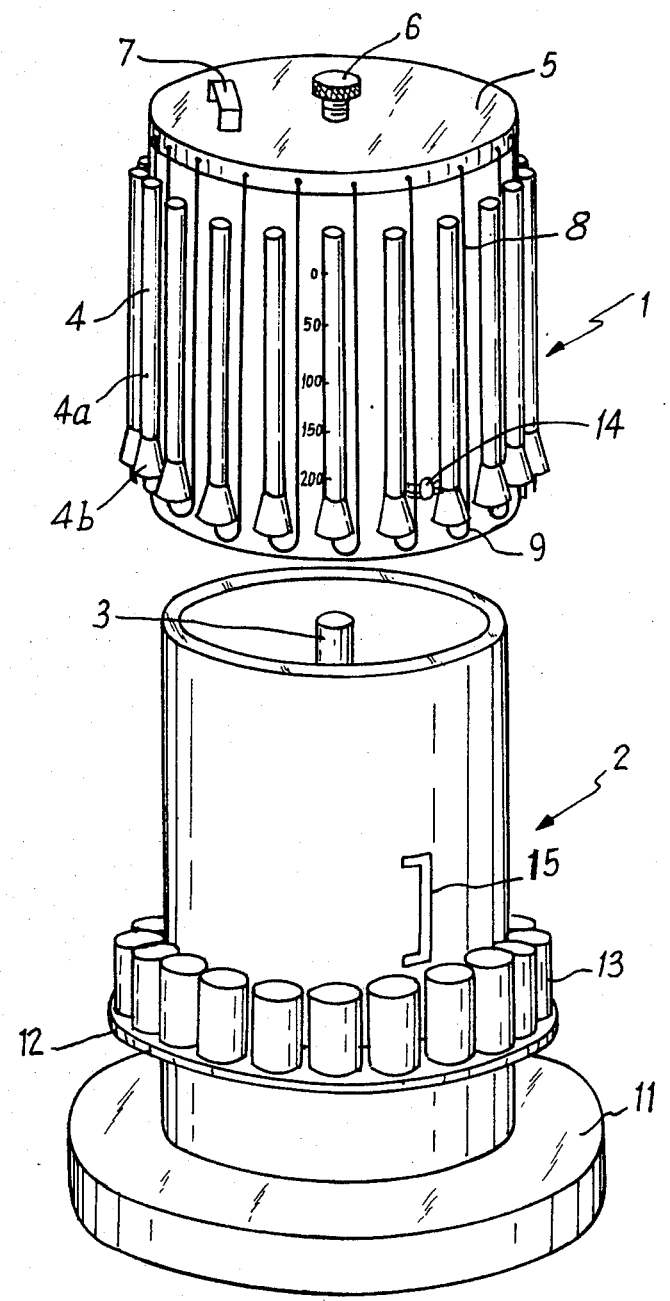

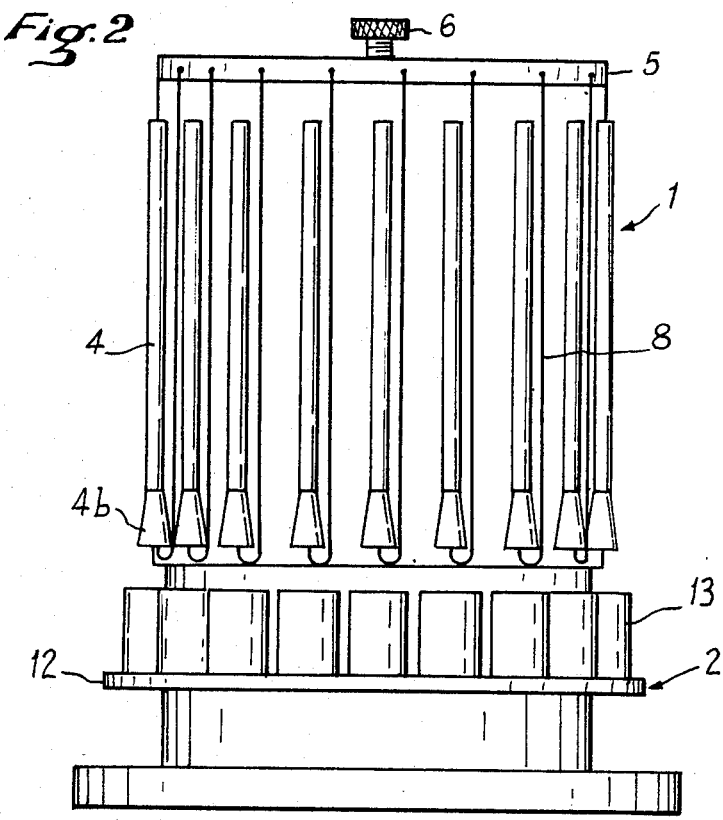
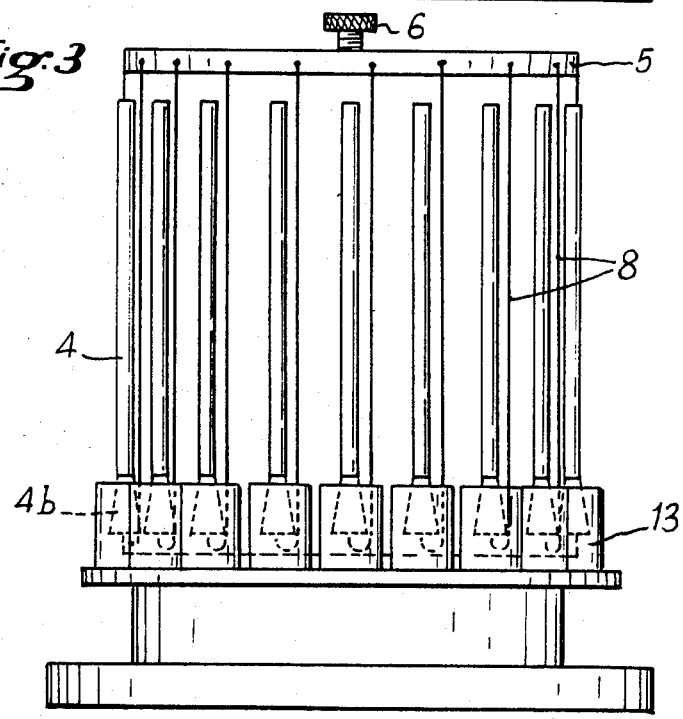

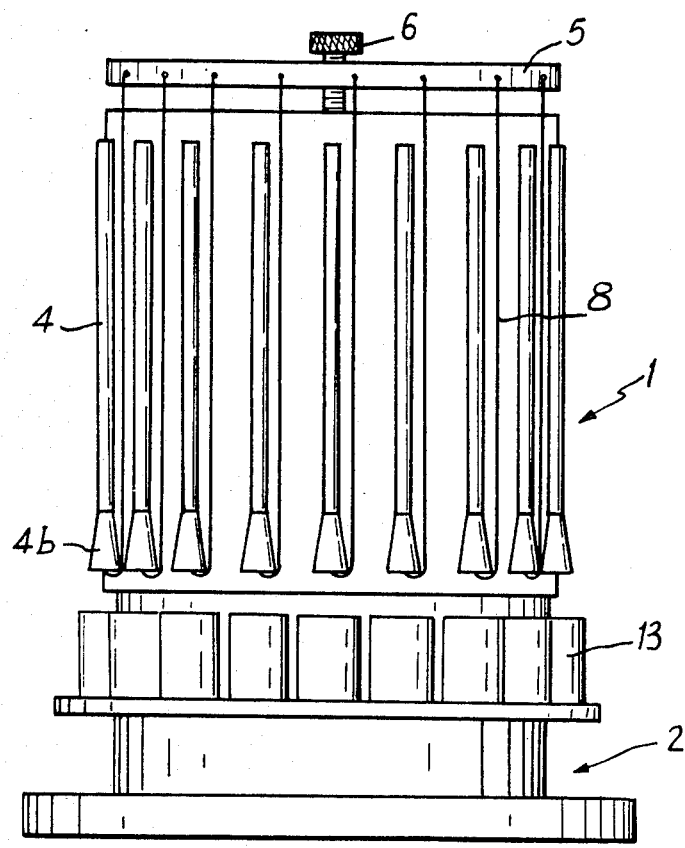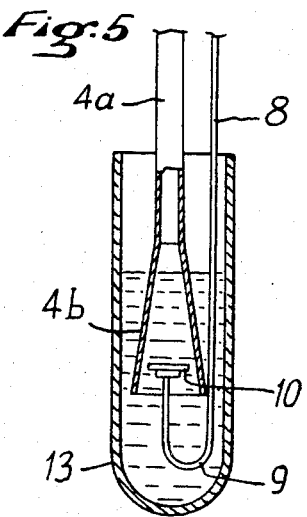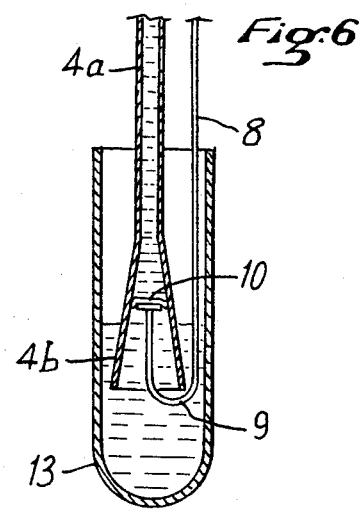

APPARATUS FOR BLOOD ANALYSIS

The present invention relates to an apparatus for medical analyses, particularly an apparatus for blood analyses to determine the sedimentation rate of corpuscles, particularly erythrocytes, and to a method for using the apparatus.

BACKGROUND OF THE INVENTION

Traditionally, sedimentation rates are measured using a Westergreen tube or pipette, that is, a thin graduated tube open at both ends. The technician first immerses such a tube in a tube or container of larger diameter containing a blood sample, then sucks up the blood from the upper end of the Westergreen tube to a predetermined upper reference graduation of the tube. The lower end of the tube is then sealed and the tube is placed on a support. The operation is repeated successively for each sample tube.

Spaced readings are then taken, the first usually at the end of one hour, and the second at the end of two hours, of the level of sedimented red blood corpuscles in each tube.

After the analysis, the used tubes are washed and cleaned for reuse.

For a medical analysis laboratory carrying out a large number of sedimentation rate measurements every day, the process thus described must be repeated as many times as there are blood samples to be analyzed. In addition to the fact that this process is relatively time-consuming, it also posed a medical danger for the technician who must draw up the blood by mouth suction from the tubes containing the samples, into the Westergreen tubes, to the appropriate level and who may, in the case of improper suction, ingest contaminated blood.

In U.S. patent application Ser. No. 560,477, filed Dec. 12, 1983 (based on French patent application No. 82 21221), applicant has already proposed a blood analysis apparatus eliminating all risk to the technician and allowing a large number of analyses to be carried out simultaneously.

SUMMARY OF THE INVENTION

The present invention provides an apparatus offering the same advantages as the apparatus described in the prior application, particularly as to safety to the technician, while being of simplified construction and operation, particularly in avoiding the use of a suction device.

The apparatus according to the invention is essentially characterized by the fact that it includes a first support means for supporting several graduated Westergreen tubes open at both ends, with their axes vertical, and horizontally spaced apart on the support means, each of the Westergreen tubes having a lower end of enlarged section, which can be tubular, but preferably diverges downwardly. A second support means has a number of tubes or containers of larger diameter than the lower ends of the tubes mounted on the first support means and which receive a blood sample, the containers being horizontally spaced on the said second support means so the Westergreen tubes are vertically aligned with the containers. The said first support means also has several closing and compressing members, each engaged in the diverging lower end of the Westergreen tubes. The two support means are movable vertically with respect to each other between a first position in which the tubes on the first support means are vertically separated from the containers on the second support means, and a second position in which the lower ends of the tubes on the first support means are immersed in the containers on the second support means. The closing and compressing members are themselves movably mounted on the first support means between a lower position spaced from the tubes on the first support means, and an upper position in contact with the inner wall of the tubes, the movement of the closing and compressing members between the lower and upper portions causing, when the support means are in their said second position, the flow or pumping of a predetermined quantity of the blood sample from the containers on the second support means into the tubes on the first support means.

In one preferred embodiment, the closing and compressing members comprise disks whose diameters correspond to the enlarged diameter of the lower portion of the tubes, when this latter is tubular. In the case of a diverging or flared portion, the diameters of the disks are between the diameter of the mouth and the main tubular body portion of the Westergreen tubes, and the disks are of an elastically deformable material.

In one particular embodiment, each of the disk shaped members is connected to a curved or U-shaped lower end of a rod which is movable vertically along the first support means, the rods being connected, preferably at their upper ends, to a support or operator which is movable vertically with respect to the first support means.

In one particularly advantageous embodiment of the invention, the support means are made in the form of cylinders or drums of circular section and the tubes are mounted around the periphery of the cylinders, the rods with the closing and compressing disks then being connected, at their upper end, to a rim or ring mounted to be moved vertically with respect to the cylinder of the first support means, advantageously by a screw thread mechanism which allows fine control of the vertical movement of the ring relative to the first support cylinder.

The apparatus according to the invention advantageously includes a cleaning tank in which the entire apparatus can be immersed after the analyses are completed, the closing and compressing or pumping members then being operated to improve the circulation of the cleaning water in the tank, through the Westergreen tubes.

Other advantages and characteristics of the invention will become apparent from the following description of wholly non-limiting embodiments, with reference to the accompanying drawings.

BRIEF DESCRIPTION OF DRAWINGS

FIG. 1 is an exploded perspective view of one embodiment of the apparatus according to the invention;

FIGS. 2 to 4 are side views showing schematically, the apparatus of FIG. 1, in three operating positions; and FIGS. 5 and 6 are enlarged views in section of the lower end of a Westergreen tube in positions corresponding to the positions of the apparatus in FIGS. 3 and 4, respectively.

DETAILED DESCRIPTION

The apparatus according to the invention shown on FIG. 1 basically includes two cylinders 1 and 2 of circular section. The upper cylinder 1 is a sliding fit on lower cylinder 2, the two cylinders thus being mounted concentrically around an axle 3.

Upper cylinder 1 supports a plurality of identical Westergreen tubes 4, for example, twenty-five in number, the tubes 4 being vertical, and spaced apart around the periphery of cylinder 1. Each tube 4 has a main tubular portion 4a extended at the lower end by a larger flared or diverging portion 4b in the shape of an inverted funnel. The lower ends of the tubes are all in the same horizontal plane perpendicular to the axis of cylinder 1.

Each tube 4 is graduated and preferably, there is also a corresponding graduation (not shown) on the wall of cylinder 1.

At the upper portion of cylinder 1 there is a support in the form of a crown or cover 5 having a peripheral rim. Crown 5 is movable vertically with respect to cylinder 1, advantageously by means of a screw 6 having a knurled adjusting knob, and passing through a threaded nut (not shown) fixed to the center of cover 5. The lower end of screw 6 is connected to a bearing fixed to cylinder 1, and at its center, so that turning the screw moves cover 5 up or down relative to cylinder 1. The screw is connected to the bearing for rotation but against axial movement, so the screw couples the cover to the cylinder 1.

Gripping handles 7 are provided on the cover 5 (only one being shown), so that the cylinder 1 can be lifted with these handles.

At the rim at the periphery of cover 5 are fastened metal rods 8, corresponding in number to the number of Westergreen tubes 4, each of the rods 8 being bent to provide U-shaped lower ends 9, and having at the end of this bent portion, as is shown at FIGS. 5 and 6, an elastically deformable disk 10 of circular section.

The disks 10 mounted at the lower ends of rods 8 constitute, as will be explained below, sealing members for the lower end of the Westergreen tubes, and flow causing or pumping members to cause a predetermined quantity of blood sample to flow upwardly into the tubes 4.

Lower cylinder 2 includes a base 11 and an annular flange 12 on which are mounted blood sample test tubes or containers 13. The number of containers 13 equals the number of Westergreen tubes 4 of first cylinder 1, that is, twenty-five in this embodiment.

According to the invention, to retain upper cylinder 1 in the predetermined relative positions with respect to lower cylinder 2, there is advantageously provided a mechanism including diametrically extending rods or pins 14 fixed to the wall of cylinder 1, and projecting inwardly, as shown at FIG. 1. The rods or pins extend into and can slide in diametrically opposed slots 15 formed in the wall of lower cylinder 2, each slot being generally C-shaped and having one vertical portion and two spaced apart horizontal portions. This arrangement permits holding the cylinder 1 in the upper position shown at FIG. 2, by engagement of pins 14 in the upper horizontal part of slot 15, and lowering cylinder 1 to the position of FIG. 3 by turning the cylinder so the pins are in the vertical part of slot 15.

One method of using the apparatus according to the invention will now be described with reference to FIGS. 2 to 6.

As is shown at FIG. 2, cylinder 1 is first placed in its upper position with respect to cylinder 2 and containers 13, containing the blood samples, are placed vertically below the respective tubes 4, on flange 12 of cylinder 2. Flange 12 can have cup-like sockets to assure vertical alignment of the containers 13 with tubes 4.

Cylinder 1 is then lowered with respect to cylinder 2 to the position shown at FIG. 3 in which the lower end of each Westergreen tube 4 of cylinder 1 is immersed in a container 13 on flange 12 of cylinder 2.

By rotating the knurled screw 6, crown 5 is lifted with respect to cylinder 1 to lift rods 8 relative to cylinder 1 to the position shown at FIG. 4.

As best shown at FIGS. 5 and 6, between the positions of FIGS. 3 and 4, the ascent of disks 10 at the ends of the lower curved parts 9 of rods 8, confines a quantity of blood in the lower diverging ends 4b of the tubes when the disks first engage the inside of the diverging ends 4b. Further upward movement of rods 8 causes the disks 10 to deform and slide upwardly along the interior wall of the diverging portions 4b to force blood upwardly into the tubular pipette portion 4a of the Westergreen tubes, the respective diameters of the tubes and the diverging portions, and the extent of movement of rim 5 being such that the blood sample in each Westergreen tube reaches a starting reference level near the upper portion of each tube. Cylinder 1 can then be lifted to the position shown at FIG. 4.

The apparatus is thus placed in the measuring position and the sedimentation level of the red blood corpuscles in tubes 4 can be noted at appropriate intervals by reading either the graduations on each of the tubes, or by reference to the graduations of the measurement scale which can be provided on the upper cylinder 1.

Once the analysis is finished, disks 10 are disengaged from tubes 4 by turning screw 6 to lower cover 5 and containers 13 are removed and the whole apparatus is placed in a tank of washing water in which tubes 4 can be flushed by circulating water in the tubes by alternating movement of rods 8 via rim 5.

The analysis can be done when the cylinder 1 is in its lower position with respect to cylinder 2, by not lifting the cylinder to the position of FIG. 4, after raising the cover by turning screw 6.

The upper ends of rods 8 can be pivotally connected to the rim of the cover so the disks 10 are self-centering in the lower ends 4b, as the disks are lifted.

Although the invention has been described in connection with particular embodiments, it is, of course, in no way thereby limited and may undergo numerous variations and modifications without departing from the scope or spirit of the invention.

I claim:

1. Blood analysis apparatus for determining sedimentation rates comprising first support means, a plurality of graduated tubes open at both ends, said tubes being mounted vertically and spaced apart on said first support means, said tubes each having a tubular body portion having a predetermined interior cross-sectional area and a lower portion extending a predetermined length downwardly from the tubular body portion and having an interior of a cross-sectional area greater than that of the tubular body portion at all lengths downward from said tubular body portion to provide a lower portion of enlarged section, second support means, a plurality of blood sample containers being of a size such that the lower portion of the tubes can be inserted therein, said containers being mounted vertically and spaced apart on said second support means, a plurality of sealing and flow causing means on said first support means engaging in the lower portion of respective tubes, said first and second support means being movable with respect to each other between a first position in which the tubes on the first support means are vertically spaced from the containers on the second support means, and a second position in which the lower portion of the tubes on the first support means are in respective containers on the second support means, means for moving said sealing and flow causing means between a lower position in which blood can enter said lower portion of the tubes, and an upper position in contact with the interior of said lower portion of the tubes to force a predetermined quantity of a blood sample from the containers upwardly into the tubes.

2. Apparatus according to claim 1 wherein said first and second support means comprise concentric cylinders.

3. Apparatus according to claim 1 wherein said sealing and flow causing means comprise means for simultaneously forcing blood upwardly into each of the tubes.

4. Apparatus according to claim 1, wherein said sealing and flow causing means comprise flexible disks.

5. Apparatus according to claim 4 wherein the lower portion of each of the tubes diverges in a downward direction.

6. Apparatus according to claim 5 wherein the tubular body portion of each tube is of circular interior cross-section and has an inside diameter, the lower diverging portion of each tube is conical and has a downwardly opening mouth of an inside diameter greater than the inside diameter of the tubular body portion, said disks are of an elastically deformable material, are circular, and have a diameter between the inside diameter of the mouth of the conical portion and the inside diameter of the tubular body portion of each of the tubes.

7. Apparatus according to claim 1 wherein said means for moving said sealing and flow causing means comprises rods having upper ends and U-shaped lower ends extending into the lower portion of said tubes.

8. Apparatus according to claim 7 wherein said rods are connected at their upper ends to means movable vertically with respect to the first support means.

9. Apparatus according to claim 8 wherein said means movable vertically comprises a rim coupled to said first support means, and means for moving the rim vertically with respect to the first support means.

10. Apparatus according to claim 9 wherein said rim moving means comprises screw adjusting means connected between said rim and said first support means.

* * * * *